United States Patent
Rafaeli et al.

(10) Patent No.: US 10,098,596 B2
(45) Date of Patent: *Oct. 16, 2018

(54) METHODS AND APPARATUS FOR IMAGING WITH DETECTORS HAVING MOVING DETECTOR HEADS

(71) Applicant: General Electric Company, Schenectady, NY (US)

(72) Inventors: Tzachi Rafaeli, Shlmenit (IL); Yaron Hefetz, Kibbutz Alomin (IL)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/612,226

(22) Filed: Jun. 2, 2017

(65) Prior Publication Data

US 2017/0265825 A1    Sep. 21, 2017

Related U.S. Application Data

(63) Continuation of application No. 15/082,929, filed on Mar. 28, 2016, now Pat. No. 9,693,744, and a continuation of application No. 14/016,943, filed on Sep. 3, 2013, now Pat. No. 9,662,079.

(51) Int. Cl.
*A61B 6/00* (2006.01)
*A61B 6/03* (2006.01)
*A61B 6/04* (2006.01)

(52) U.S. Cl.
CPC ............ *A61B 6/4266* (2013.01); *A61B 6/032* (2013.01); *A61B 6/0407* (2013.01); *A61B 6/4014* (2013.01); *A61B 6/4452* (2013.01); *A61B 6/037* (2013.01)

(58) Field of Classification Search
CPC ..... A61B 6/4266; A61B 6/4452; A61B 6/032; A61B 6/0407; A61B 6/037; A61B 6/4014
See application file for complete search history.

(56) References Cited

U.S. PATENT DOCUMENTS

| | | |
|---|---|---|
| 5,287,546 A | 2/1994 | Tesic et al. |
| 5,534,701 A | 7/1996 | Pierfitte et al. |
| 5,838,009 A | 11/1998 | Plummer et al. |
| 6,631,285 B2 | 10/2003 | Natterer et al. |
| 2006/0261277 A1 | 11/2006 | D'Ambrosio et al. |
| 2008/0029704 A1 | 2/2008 | Hefetz et al. |
| 2010/0061509 A1 | 3/2010 | D'Ambrosio et al. |

*Primary Examiner* — Peter Luong
(74) *Attorney, Agent, or Firm* — Dean D. Small; The Small Patent Law Group, LLC

(57) ABSTRACT

Methods and apparatus for imaging with detectors having moving heads are provided. One apparatus includes a gantry and a plurality of detector units mounted to the gantry. At least some of the plurality of detector units are movable relative to the gantry to position one or more of the detector units with respect to a subject. The detector units are movable along parallel axes with respect to each other.

20 Claims, 14 Drawing Sheets

METHODS AND APPARATUS FOR IMAGING WITH DETECTORS HAVING MOVING DETECTOR HEADS

CROSS-REFERENCE TO RELATED APPLICATIONS

This application is a Continuation, and claims priority to and the benefit of the filing date of U.S. application Ser. No. 14/016,943, filed Sep. 3, 2013, (now U.S. Pat. No. 9,662, 079) and U.S. application Ser. No. 15/082,929, filed Mar. 28, 2016, the subject matter of which are herein incorporated by reference in their entirety.

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data.

In NM imaging systems, the resolution of the detector, in particular the gamma detector, is determined by the resolution of the detector (based on the size of pixels of the detector) and the resolution of a collimator attached to the detector. The resolution degrades with distance of the detector, specifically the collimator, from the subject.

In Single Photon Emission Computed Tomography (SPECT) systems having moving detector heads, the detectors may be positioned to focus on a region of interest. For example, a number of pinhole gamma cameras may be positioned to view a small region of interest (e.g., heart of the subject). However, these moving detector heads are not configured to operate, for example, move in such a manner to allow general purpose imaging, such as of the entire subject. For example, because of the size and spacing of the detector heads, when imaging a smaller subject, the detector heads may collide when moved in close proximity to the subject, thereby preventing placement of the detector heads close to the subject. Moreover, for larger subjects, gaps may exist between the detectors because the detectors have to be moved apart to allow for focusing on the field of view. Accordingly, because the detector heads cannot be moved in close proximity to the subject or as a result of the gaps between the detector heads, image resolution is reduced.

BRIEF DESCRIPTION OF THE INVENTION

In one embodiment, an imaging system is provided that includes a gantry and a plurality of detector units mounted to the gantry. At least some of the plurality of detector units are movable relative to the gantry to position one or more of the detector units with respect to a subject. The detector units are movable along parallel axes with respect to each other.

In another embodiment, a Nuclear Medicine (NM) imaging system is provided that includes a gantry and a pair of opposing support members coupled to the gantry, wherein the support members are on opposite sides of the gantry and in parallel alignment with each other. The NM imaging system further includes a plurality of movable detector carriers coupled to each of the support members, with each of the plurality of movable detector carriers having a proximate end coupled to a respective support member and a distal end. The plurality of movable detector carriers extend from the respective support member and are aligned in parallel with each other along the support member. The NM imaging system also includes at least one detector unit coupled to each of the distal ends of the plurality of movable detector carriers, wherein the detector units are rotatable about the distal end of the movable detector carrier. The movable detector members are configured to move the detector unit coupled thereto away from and towards the gantry.

In another embodiment, a method of imaging is provided that includes controlling movement of one or more support members coupled to a gantry to position one or more detector arrays relative to a patient table. The meth further includes controlling movement of one or more detector units of the detector array to further position the one or more detector units relative to the patient table, wherein the one or more detector units are coupled to a plurality of movable detector carriers having parallel axis of movement with respect to each other. The method also includes acquiring image data using the one or more detector units, wherein acquiring the image data comprises rotating the one or more detector units relative to the movable detector carriers.

DETAILED DESCRIPTION OF THE INVENTION

Figure 1:
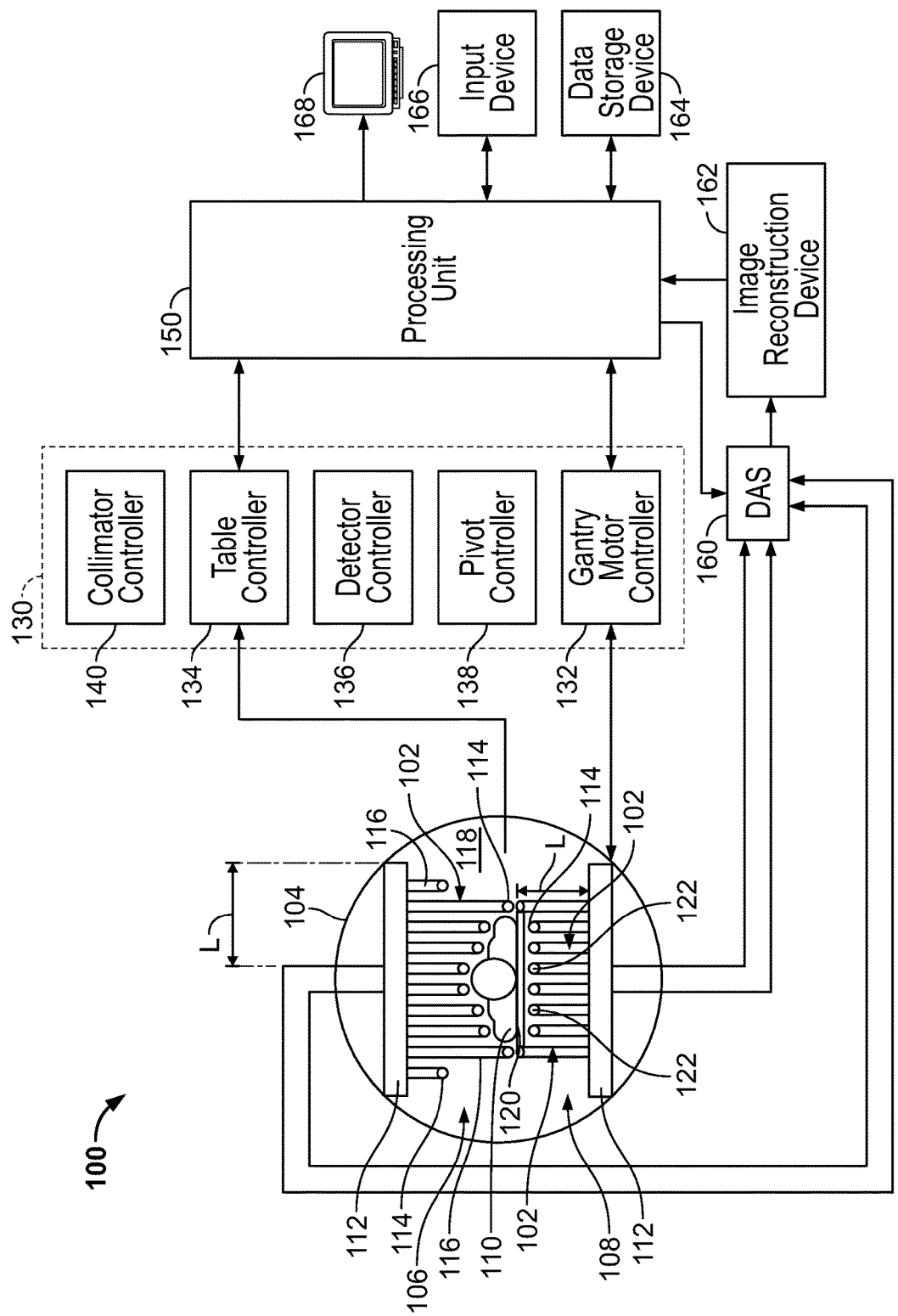
FIG. 1 is a schematic block diagram of a Nuclear Medicine (NM) imaging system in accordance with an embodiment.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide apparatus and methods for controlling the movement of a plurality of imaging detectors to position the imaging detectors adjacent subjects, such as patients of different sizes. For example, in various embodiments a general purpose Nuclear Medicine (NM) camera with an array of heads that are individually and independently movable is provided. In some embodiments, one or more of the heads are capable of a plurality of types of movement, such as rotation and parallel linear motion. For example, the detector heads may be configured to move downwards and/or towards a subject in parallel planes or along parallel axes (e.g., comb like movement) instead of radial motion toward the center of a gantry. By practicing various embodiments, efficient placement of detector heads around subjects of different sizes and shapes is provided, such that resolution and sensitivity are increased or maximized.

FIG. 1 is a schematic illustration of a Nuclear Medicine (NM) imaging system 100 having a plurality of imaging detectors mounted on a gantry. In particular, a plurality of imaging detectors 102 are mounted to a gantry 104. In the illustrated embodiment, the imaging detectors 102 are configured as two separate detector arrays 106 and 108 coupled to the gantry 104 above and below a subject 110 (e.g., a patient), as viewed in FIG. 1. The detector arrays 106 and 108 may be coupled directly to the gantry 104, or may be coupled via support members 112 to the gantry 104 to allow movement of the entire arrays 106 and/or 108 relative to the gantry 104 (e.g., translating movement in the left or right direction as viewed in FIG. 1). Additionally, each of the imaging detectors 102 includes a detector unit 114 mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly and in parallel to each other. Thus, in the illustrated embodiment the detector arrays 106 and 108 are mounted in parallel above and below the subject 110 and allow linear movement of the detector units 114 in a single direction (indicated by the arrow L), illustrated as perpendicular to the support member 112 (that are coupled generally horizontally on the gantry 104). However, other configurations and orientations are possible as described herein.

Each of the imaging detectors 102 in various embodiments are smaller than a conventional whole body or general purpose imaging detector. A conventional imaging detector may be large enough to image most or all of a width of a patient's body at one time and may have a diameter of approximately 40 cm. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 110 may be formed with an aperture 118 (e.g., opening or bore) therethrough as illustrated. A patient table 120 is configured with a support mechanism (not shown) to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each of the imaging detectors 102 has a radiation detection face, which is directed towards the subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator. In some embodiments, at least two types of collimators are used.

Optionally, multi-bore collimators may be constructed to be registered with pixels of the detector units 114, which in one embodiment are CZT detectors. However, other materials may be used. Registered collimation may increase spatial resolution by forcing photons going through one bore to be collected primarily by one pixel. Additionally, registered collimation may increase sensitivity and energy response of pixelated detectors as detector area near the edges of a pixel or inbetween two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 110, imaging detectors 102, gantry 104 and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow coordinated move of the detector array 106 or 108. For example, the detector controller 136 may control lateral movement of the detector carriers 116 illustrated by the L arrow (and shown as left and right as viewed in FIG. 1). In some embodiments, proximity sensors may be used to guide the controllers to bring the detectors 102 in proximity to (e.g., within close range, such as 1-5 cm) from the subject 110 without colliding with or contacting the subject 110. Alternatively or additionally, the shape of the subject 110 (e.g., patient shape) may be known from imaging the subject 110 with another modality such as CT or 3D optical imaging and the information regarding the shape of the subject 110 used to position the detectors 102. Optionally, in some embodiments, at least some of the detectors 102 include a Pressure Sensing Device (PSD) capable of detecting physical contact of a sensor with the subject 110 or other solid objects and prevent or halt motion of at least one of the detectors 102, patient bed 120, or gantry 104 that may, for example, cause harm to the subject 110.

The pivot controller 138 may control pivoting movement of the detector units 114 at ends of the detector carriers 116 and/or pivoting movement of the detector carrier 116. For example, one or more of the detector units 114 or detector carriers 116 may be rotated about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 110, gantry 104, patient table 120 and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector arrays 106 and 108, which as illustrated in FIG. 1 are in a retracted position away from the subject 110. Positioning may be accomplished manually by the operator and/or automatically, which may include using other images acquired before the current acquisition, such as by another imaging modality such as CT, MRI, X-Ray, PET or ultrasound. Additionally, the detector units 114 may be configured to acquire non-NM data, such as x-ray CT data.

After the imaging detectors 102, gantry 104, patient table 120, and/or collimators 122 are positioned, one or more images are acquired by one or more of the imaging detectors 102 being used. The image data acquired by each imaging detector 102 may be combined and reconstructed into a composite image, which may comprise two-dimensional (2D) images, a three-dimensional (3D) volume or a 3D volume over time (4D).

In one embodiment, the imaging detectors 102, gantry 104, patient table 120, and/or collimators 122 remain stationary after being initially positioned. In another embodiment, an effective field of view for one or more of the imaging detectors may be increased by movement such as pivoting one or more of the imaging detectors 102, rotating one or more of the detector arrays 106 and/or 108 with the gantry 110, adjusting one or more of the collimators 122, or moving the patient table 120.

In various embodiments, a data acquisition system (DAS) 160 receives electrical signal data produced by the imaging detectors 102 and converts this data into digital signals for subsequent processing. An image reconstruction device 162 and a data storage device 164 may be provided in addition to the processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images.

Figure 2:
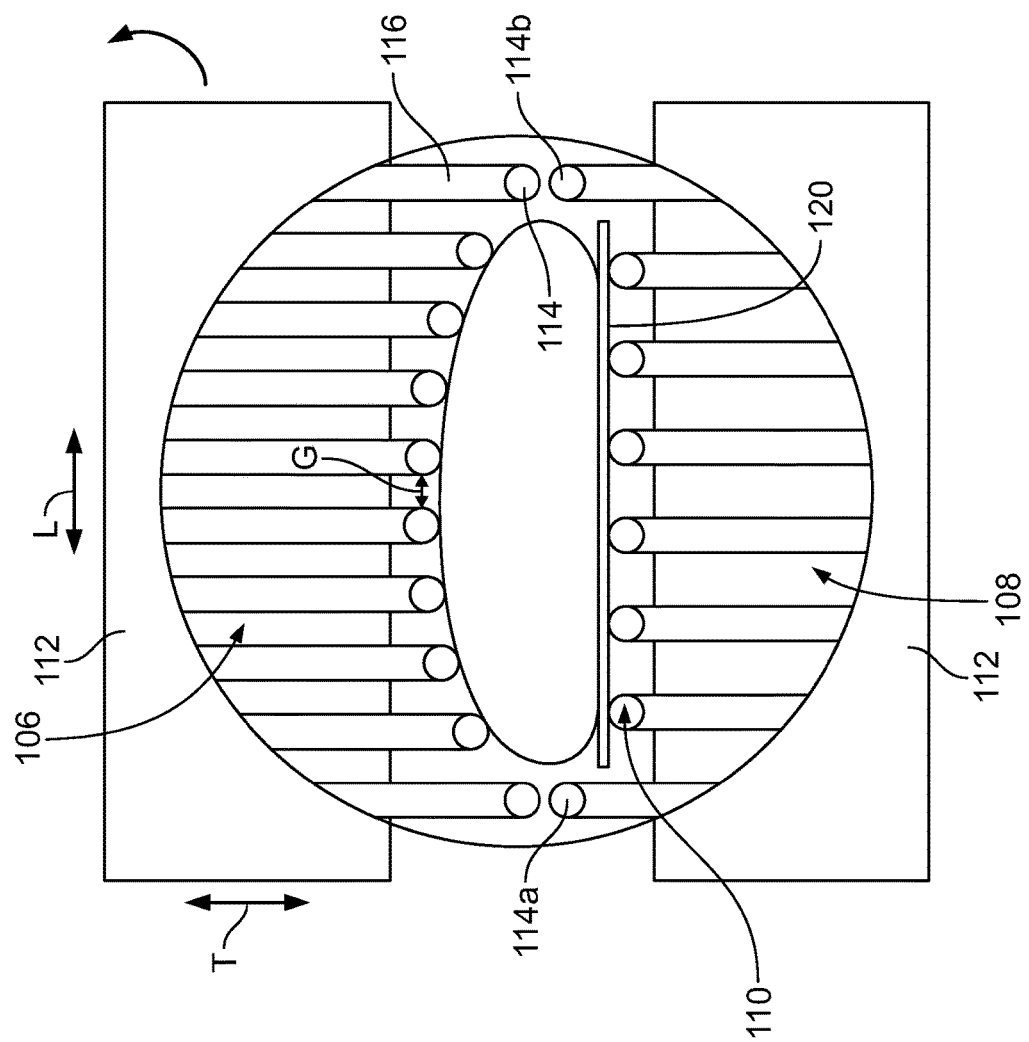
FIG. 2 is a schematic block diagram illustrating movement of detector units in accordance with an embodiment.

In operation, and as shown, for example, in FIG. 2, one embodiment includes two detector arrays 106 and 108 (in opposed parallel alignment) that allow movement of a plurality of detector units 114, illustrated as detector heads at the distal ends of a plurality of the detector carriers 116. In this embodiment, the two detector arrays 106 and 108 are top and bottom detector arrays, respectively, wherein the subject 110 is positioned therebetween on the patient table 120 with the detector array 106 above the subject 110 and the detector array 108 below the subject 110. As can be seen, the detector units 114 of the detector arrays 106 or 108 are generally supported along a plane of the support member 112 and moveable relative thereto. For example, the support members 112 may be generally planar with each of the detector units 114 moveable with respect to the support member 112 such that the detector units 114 move along parallel axes relative to the plane of the support member 112 (e.g., perpendicular to the plane of the support member 112 while maintaining a parallel relationship). In some embodiments, the support members 112 of the detector arrays 106 and 108 are also arranged in an H-type configuration or parallel to each other. In one embodiment, the lower support member 112 is coupled to the patient bed 120 (or other bed support) such that lower support member 112 moves up and down with the patient bed 120. Alternatively, in some embodiments, the lower support member 112 is configured to move in unison with the up/down bed motion (e.g., moved simultaneously or concurrently with the patient bed 120), but may not be coupled to the patient bed 120.

In this embodiment, each of the detector units 114 of the detector array 106 is individually and independently controllable to translate the detector units 114 upwards and downwards with respect to the subject 110. For example, one or more of the detector units 114 in the detector array 106 is operable to translate down until the detector unit 114 is proximate or adjacent the subject's body, while not contacting or colliding with the subject 110. The distance of the detector units 114 from the subject 110 may be controlled using one or more proximity sensors as known in the art. Thus, as shown in FIG. 2, a plurality of the detector units 114 of the detector array 106 is moved towards and positioned proximate or adjacent the subject 110 (wherein some of the detector units 112 are positioned at different distances from the support member 112 than other detector units 112).

It should be noted that optionally the support member 112 may be moved to facilitate positioning of the detector units 114. For example, depending on the size of the subject 110 and the maximum length of the detector carriers 116, the support member 112 of the detector array 106 may likewise move towards or away from the subject 110 (as illustrated by the T arrow), such that all of the detector units 114 are moved together to a position closer or farther from the subject 110 (e.g., coarse movement) with the individual detector units 114 thereafter moved to position each in proximity or adjacent to the subject 110 (e.g., fine tuning movement). The support members 112 also may provide other optional movement, such as later movement (left and right as viewed in FIG. 1) as illustrated by the L arrow. For example, depending on the size or shape of the subject 110 and the positioning of the patient table 120, the support member 112 may initially translate to align the detector array 106 in a direction parallel to the coronal plane of the subject 120.

The detector units 114 in the detector array 108 in the illustrated embodiment are in a fixed position relative to the patient bed 120. For example, the detector units 114 may be fixedly mounted to the gantry 104 or to the support member 112 below the subject 110. In some embodiments, the detector carriers 116 are provided and may be fixed such that translating movement is not provided. In other embodiments, the detector carriers 116 are not provided with the detector units 114 fixedly mounted directly or through another fastening means (e.g., bracket) to the gantry 104 or to the support member 112 below the subject 110. However, in other embodiments the detector units 114 below the subject 110 may be movable with respect to the patient table 110. In various embodiments, the detector units 114 below the subject 120 are still individually rotatable or tiltable, while in other embodiments no movement is provided. Thus, the detector units 114 below the subject 110 may be movable or non-movable.

It should be noted that the positioning of the plurality of detector units 114, in particular each of the individual detector units 114 in the detector array 106 and/or 108 may be provided at the same time (e.g., concurrently or simultaneously) or at different times (e.g., sequentially).

In operation, once positioned, one or more of the detector units 114 of the detector array 106 may rotate, for example, along the examination axis and/or transverse (e.g., perpendicular) to the examination axis to view the subject 110 from a plurality of different orientations. The movement of the detector units 114 may be, for example, stepwise or continuous through a range of motion. The detector units 114 of the detector array 108 likewise may rotate. The detector units 114 of the detector arrays 106 and 108 may rotate at the same time (e.g., concurrently or simultaneously) or may rotate at different times (e.g., sequentially).

It should be noted that variations and modifications are contemplated. For example, as illustrated in FIG. 2, one of more edge detector units 114a and 114b (two are illustrated, one at each end of the detector array 108) optionally may be located outside the edge of the patient table 120 such that movement from below the patient table 120 to a position above the patient table 120 (e.g., adjacent a side of the subject 110) may be provided. The detector units 114a and 114b may be positioned orthogonally with respect to the detector carrier 116 to point sideways towards the subject 110. In one embodiment, the other detector units 114 of the detector array 108 are fixed, while in other embodiments one or more of the other detector units 114 may be configured for movement as described herein.

Thus, in operation, the parallel movement of the detector units 114 in the detector array 106 above the subject 110 and with respect to each other allows positioning of the detector units 114 relative to any size subject 110. For example, each of the detector units 114 may be individually translated downward to be positioned in proximity or adjacent to a portion of the patient 110. Additionally, because the detector units 114 within the detector array 106 or 108 move along the same parallel planes (e.g., upwards and downwards in respective linear directions), the detector units 114 may be positioned with respect to subjects 110 having different sizes and shapes, while maintaining the same lateral gap (G) between each of the detector units 114. In various embodiments, an increased number of detector units 114 then may be used when imaging a larger subject 110.

Figure 3:
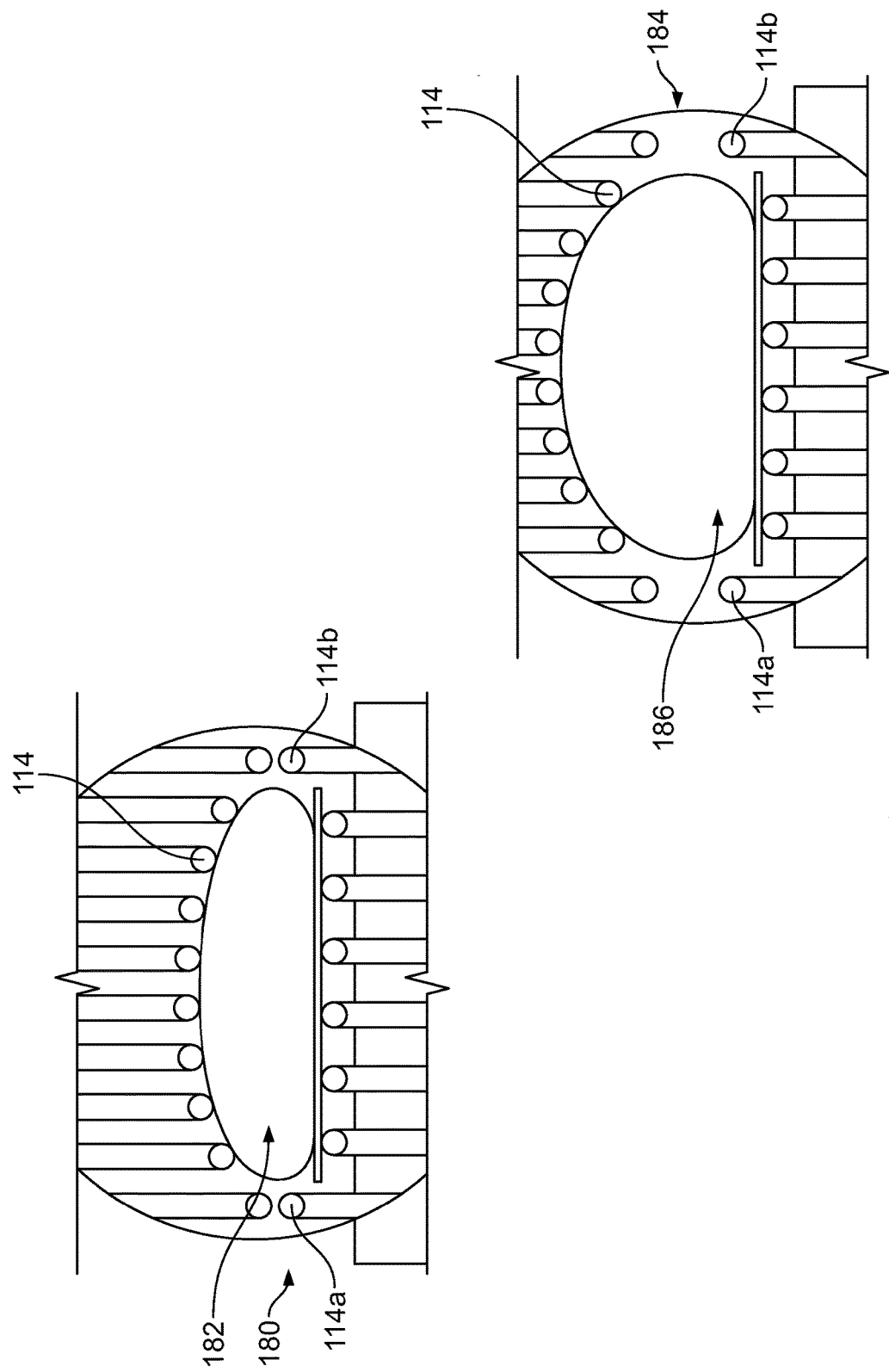
FIG. 3 is a schematic block diagram illustrating detector unit positioning for different sizes of subjects in accordance with an embodiment.
Figure 4:
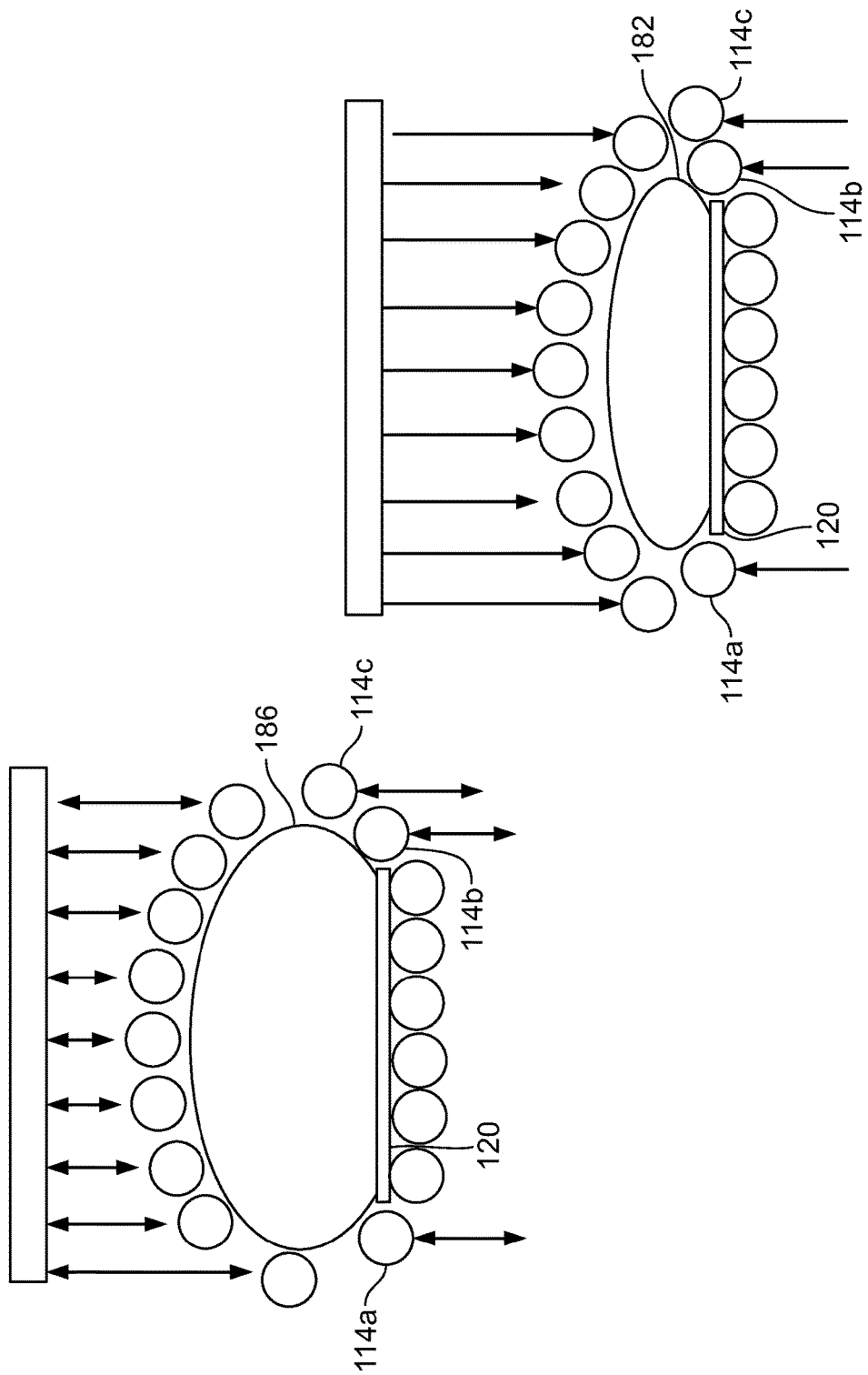
FIG. 4 is a schematic block diagram illustrating detector unit positioning for different sizes of subjects in accordance with another embodiment.

For example, as shown in FIG. 3, the detector units 114 may be individually moved to be positioned adjacent either a smaller subject 182 or a larger subject 186 in the configurations 180 and 184, respectively. As can be seen, the same number of detector units 114 may be used whether the subject 182 or 186 is smaller or larger. Additionally, as shown in FIG. 4, the edge detector units 114a and 114b, as well as the edge detector unit 114c in this embodiment (which is adjacent the edge detection unit 114b) may be positioned on the side of the subject 182 and 186 at a height above the patient table 120. Additionally, as can be seen, one or more of the detector units 114 of the detector array 106 may extend downward along a side of the subject 182 or 186 as well to be generally adjacent one or more of the edge detector units 114a, 114b or 114c to provide coverage around the subject 182 or 186 (although some spacing may result due to the size or shape of the subject 120). It should be noted that in the illustrated embodiment, the other detector units 114 of the detector array 108 located below the patient table 120 are coupled in a fixed position with respect to the patient table 120, but may rotate as described in more detail herein.

Figure 5:
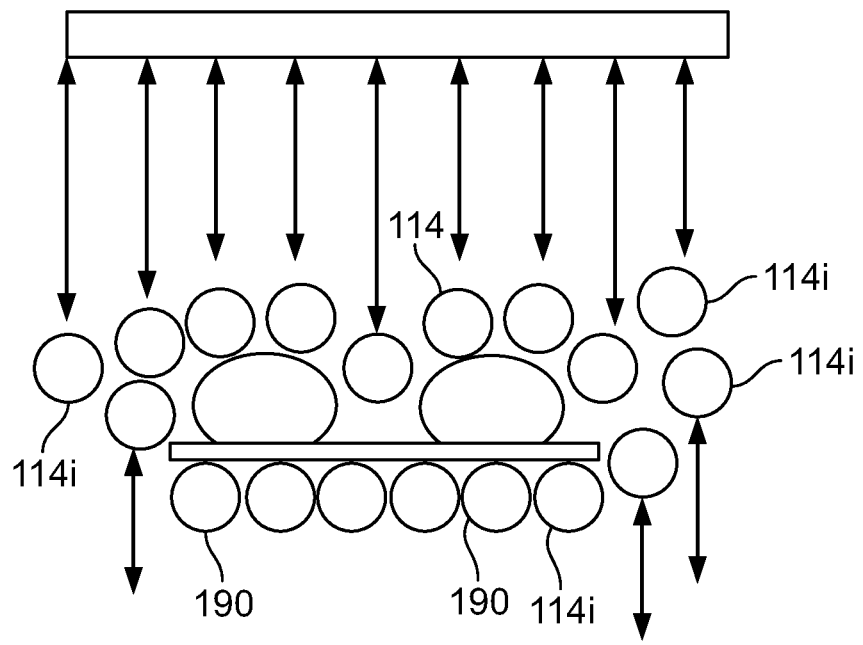
FIG. 5 is a schematic block diagram illustrating detector unit positioning for breasts of a subject in accordance with an embodiment.
Figure 6:
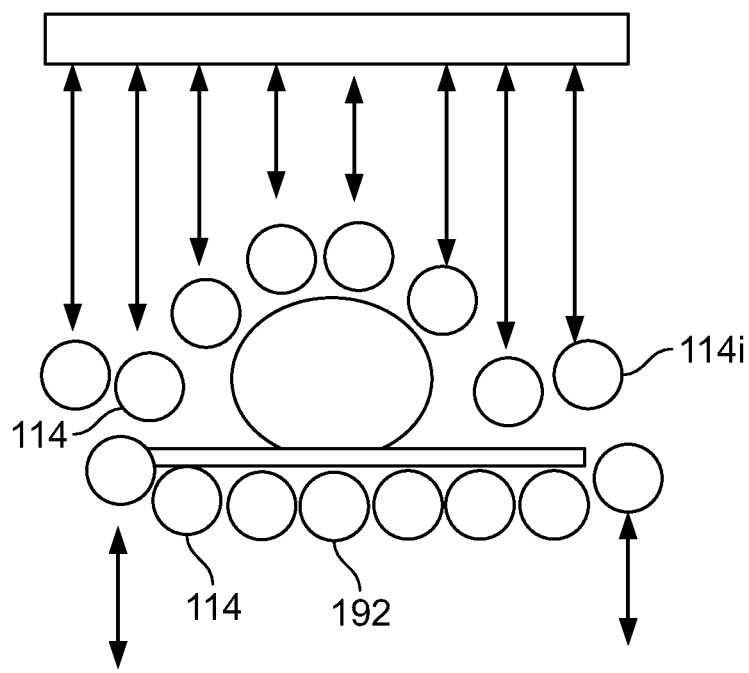
FIG. 6 is a schematic block diagram illustrating detector unit positioning for a head of a subject in accordance with an embodiment.

Different configurations also allow for imaging and coverage of smaller organs. For example, as shown in FIG. 5, the detector units 114 may be positioned proximate breasts 190 of the subject 110. As can be seen, the detector units 114 of the detector array 106 may be positioned surrounding at least a portion of the breasts 190. It should be noted that not all of the detector units 114 are needed for imaging and as such the detector units 114i are inactive and do not collect data during imaging. Additionally, while the inactive detector units 114i are shown in an extended position, the inactive detector units 114i may be in a non-extended or retracted position, for example, not moved downward as illustrated in FIG. 5. The inactive detector units 114i are shown extended merely to illustrate that other detector units 114 provide the appropriate coverage. It also should be noted that other small organs or portions may similarly be imaged, such as arms, legs, knees, head, neck, small children and newborns, etc. As another example, a head 192 may be imaged as illustrated in FIG. 6, which may be an adult, child, or infant's head. As discussed in more detail herein, the detector units 114 are moveable for positioning adjacent or proximate the head 192. Again, one or more inactive detector units 114i may result.

Figure 7:
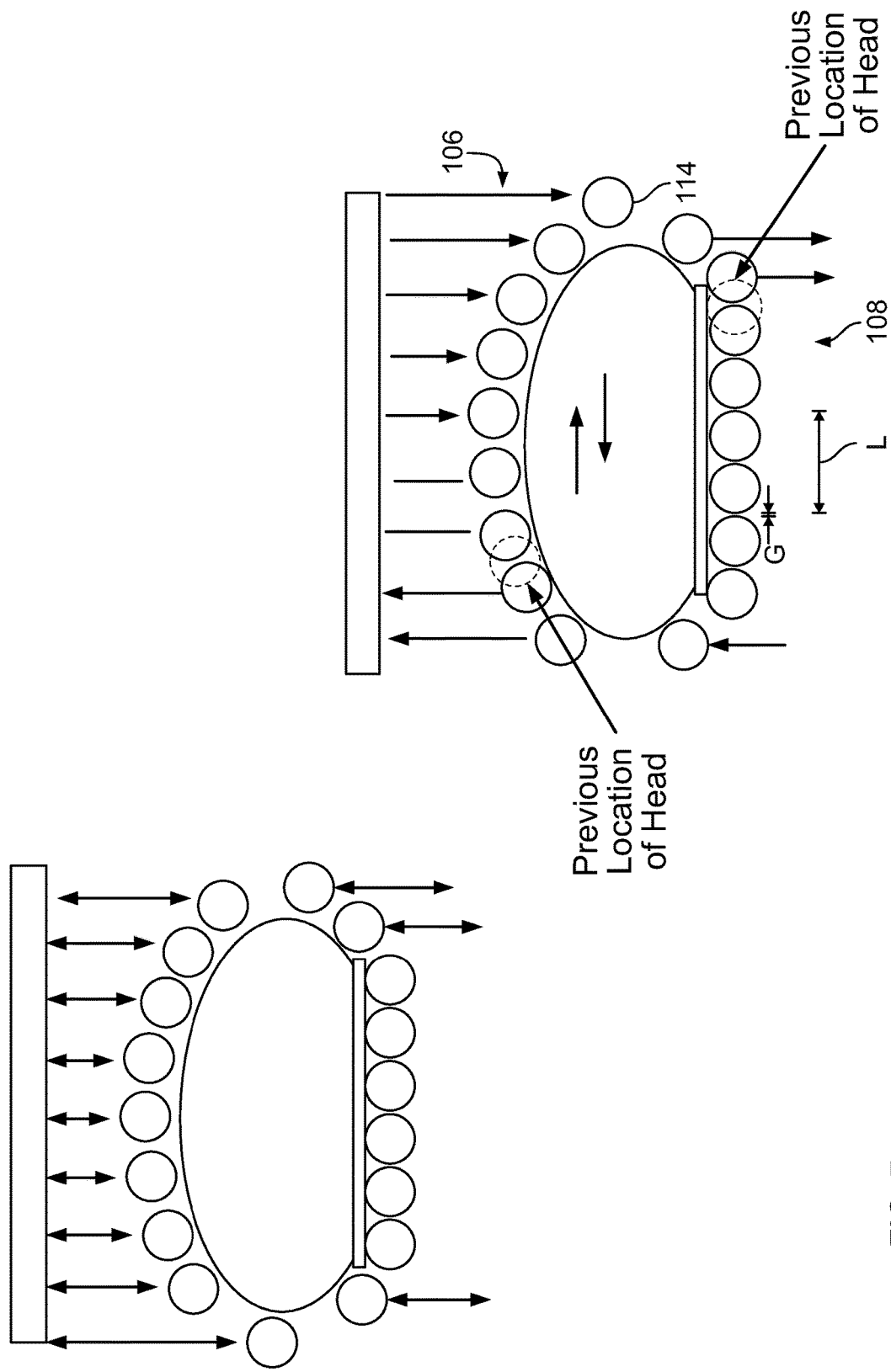
FIG. 7 is a schematic block diagram illustrating movement of detector units in accordance with another embodiment.

Additionally, as described herein the detector units 114 in the detector array 106 or 108 may be configured to move laterally (side to side). For example, as shown in FIG. 7, while the detector units 114 of the detector array 108 under the patient table 120 are coupled thereto such that no movement upwards or downwards is provided, the detector units 114 may move laterally (as indicated by the L arrow). For example, the support member 112 (shown in FIG. 1) of the detector array 108 may move the detector units 114 laterally (movement of one of the detector nits 114 is illustrated in phantom lines). In other embodiments, the detector units 114 may be configured for individual and independent lateral movement. Accordingly, in operation, the detector units 114 are shifted left or right a distance to encompass the gap therebetween. Thus, additional coverage or new angles of view may be provided.

For example, the detector units 114 may move 1/2 the detector width in some embodiments, such that imaging in the two positions doubles the sampling. Similar lateral movement of the detector units 114 of the detector array may be provided. It should be noted that the detector units 114 of the detector array 106 or the edge detector units 114 of the detector array 108 may be moved upwards or downwards in combination with the lateral movement so as to not contact the subject 110. It should be noted that SPECT reconstruction takes advantage of data obtained from a plurality of viewing points relative to the subject 110. Thus, for example, lateral motion of the detector array increases the effective number of such viewing points and thus may improve the quality of the reconstructed image. For example, the acquisition time may be divided into N (N may be chosen to be a small number such as 2, 3, or more) segments. After the data has been acquired during an acquisition segment, at least one of the detector arrays may be laterally moved and the next acquisition segment started or commenced. Optionally, in some embodiments, the lateral motion between acquisition segments is equal or approximately 1/N of the lateral distance between adjacent imaging detectors 102. During lateral motion the detector carriers may be activated to prevent collision of the imaging detectors 102 with the subject 110 or other structures, and/or to maintain close proximity to the subject 110. Optionally, in some embodiments, the duration of acquisition segments and the lateral motion between acquisition segments is not the same. Optionally, in some embodiments, the lateral motion is a continuous motion (e.g., slow continuous motion) and acquisition continues throughout the lateral motion while associating the acquired data with the location of acquisition (e.g., a record is kept associating the acquired data with the location of the detectors 102).

Figure 8:
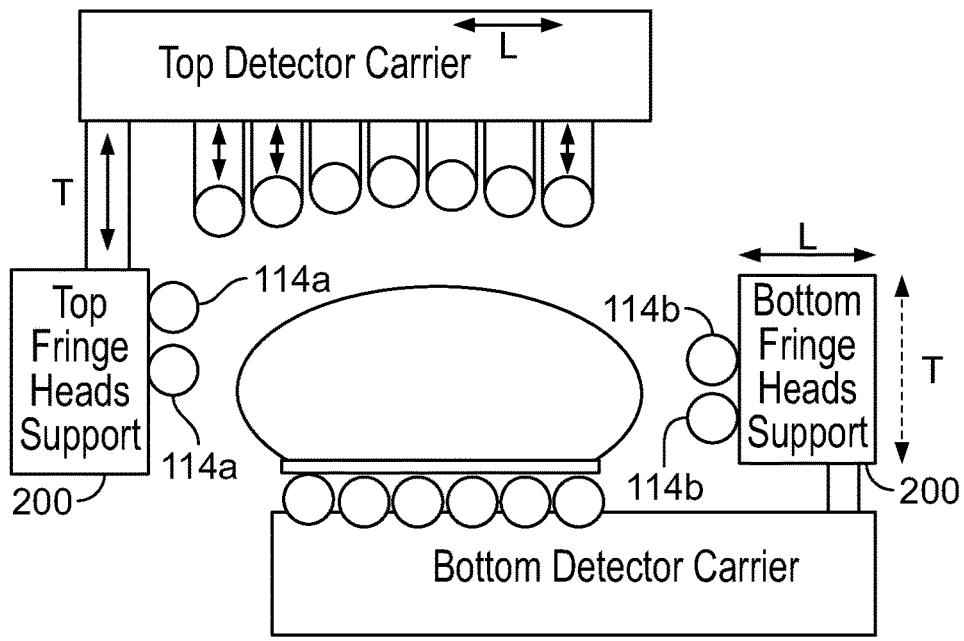
FIG. 8 is a schematic block diagram illustrating additional detector unit supports in accordance with an embodiment in one position.
Figure 9:
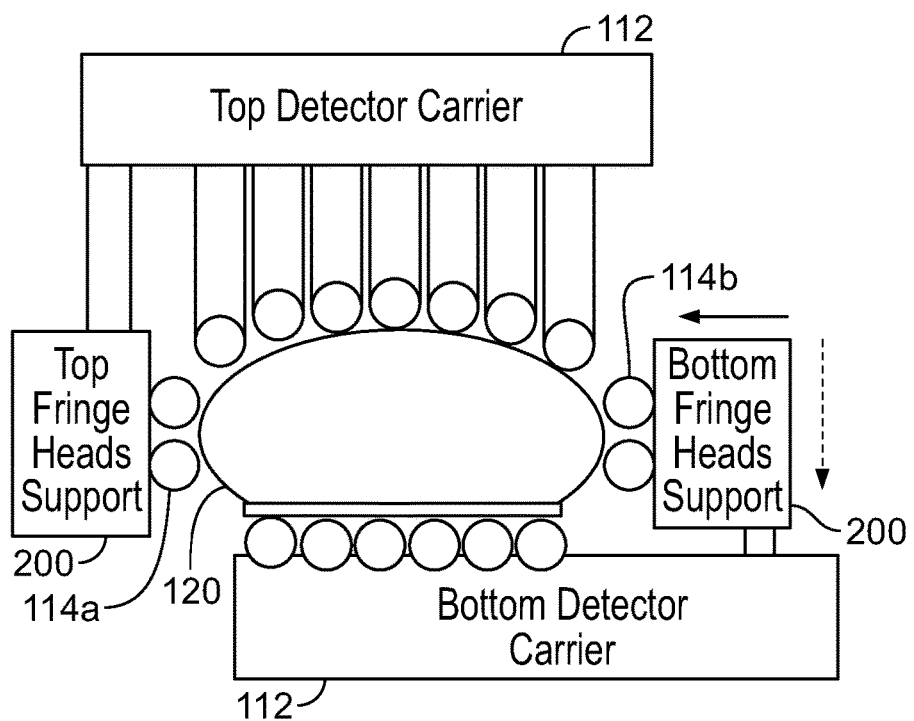
FIG. 9 is a schematic block diagram illustrating the additional detector unit supports of FIG. 8 in another position.
Figure 10:
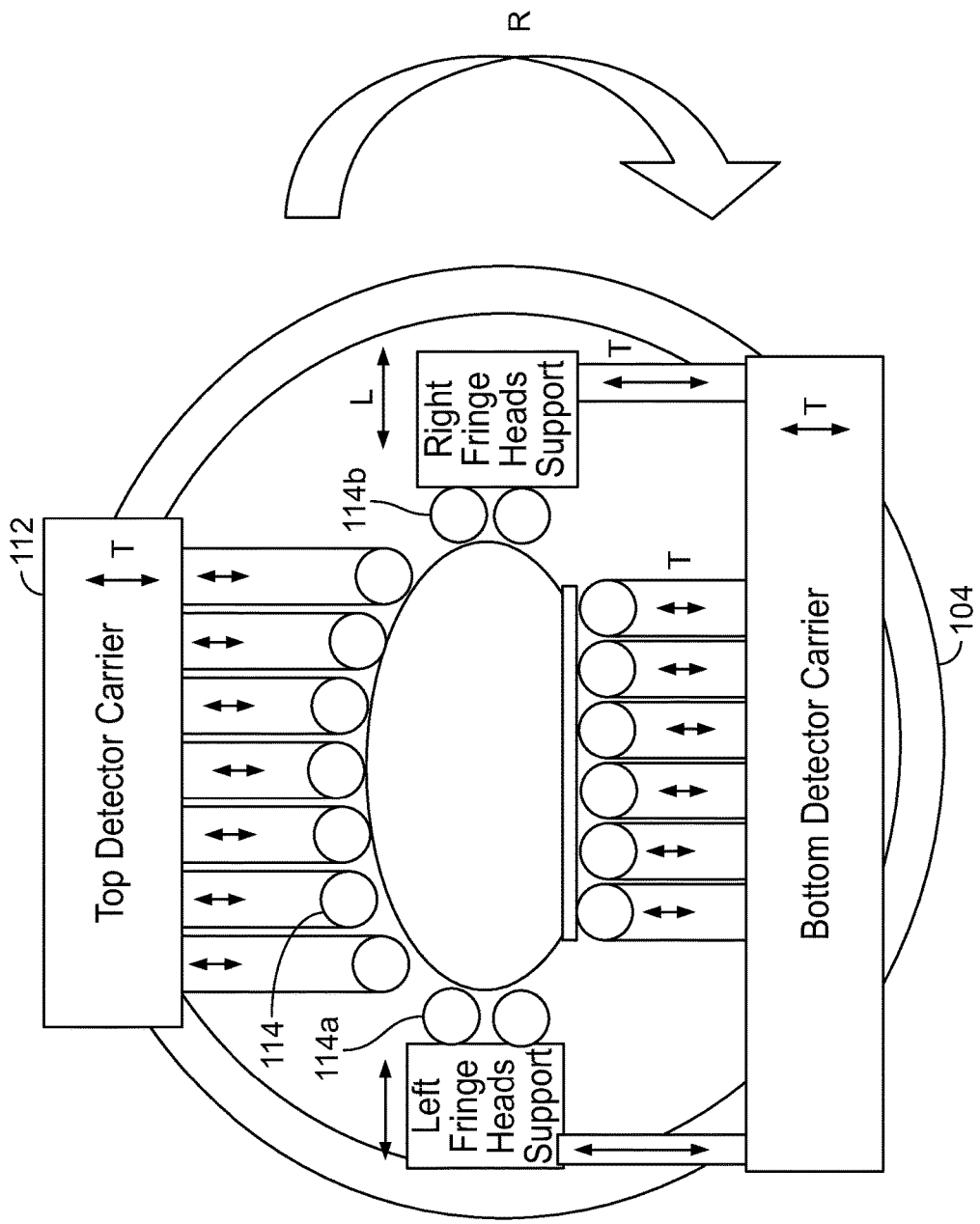
FIG. 10 is a schematic block diagram illustrating movement of detector units in accordance with another embodiment in one position.

As shown in FIG. 8, the support members 112 may support respective detector units 114, as well as an edge head support 200 on one or both ends of the support members 112. In the illustrated embodiment, the edge head support 200 is positioned on opposite ends of the top and bottom support members 112. The edge head support 200 in the illustrated embodiment extends from the support members 112 (e.g., perpendicular thereto) with edge detector units 114a and 114b positioned on a side thereof to face the subject 110. The edge head support 200 may be configured to move at least one of upwards and downwards (as illustrated by the T arrow) or laterally (as illustrated by the L arrow) with respect to the respective support member 112. Thus, the edge detector units 114a and 114b may be provided with one or more additional movement axes relative to the other detector units 114, such as to accommodate subjects 110 that are wider or larger. FIG. 9 illustrates the edge head support 200 moved to position the edge detector units 114 adjacent the subject 110. It should be noted that only one edge head support 200 may be provided or both of the edge head supports 200 may be coupled to one of the support members 112, for example, the support member 112 above or below the subject 110.

Figure 11:
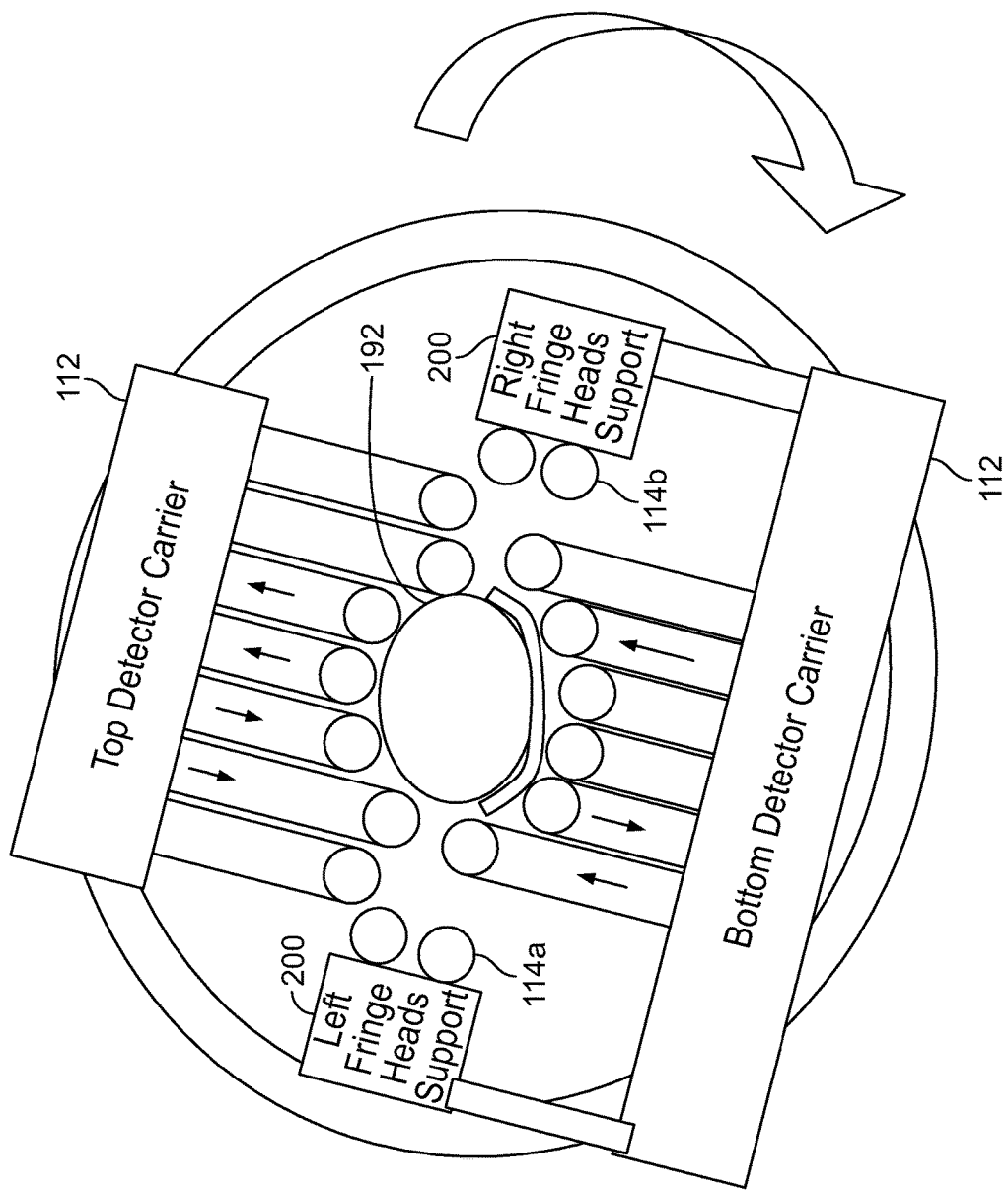
FIG. 11 is a schematic block diagram illustrating movement of detector units of FIG. 10 in another position.

Other variations are contemplated. For example, the lower support member 112 below the subject 110 may be configured for upward and downward movement (as illustrated by the T arrow). Optionally, lateral movement of the lower support member 112 may be provided. In this embodiment, the gantry 104 also may rotate the imaging detectors 102 about the subject 110 as illustrated by the R arrow. Thus, as illustrated in FIG. 11, the detector units 114 may be positioned in different radial positions around the subject 110, which may include translating movement of the detector units 114 to avoid contact with the subject 110.

Figure 12:
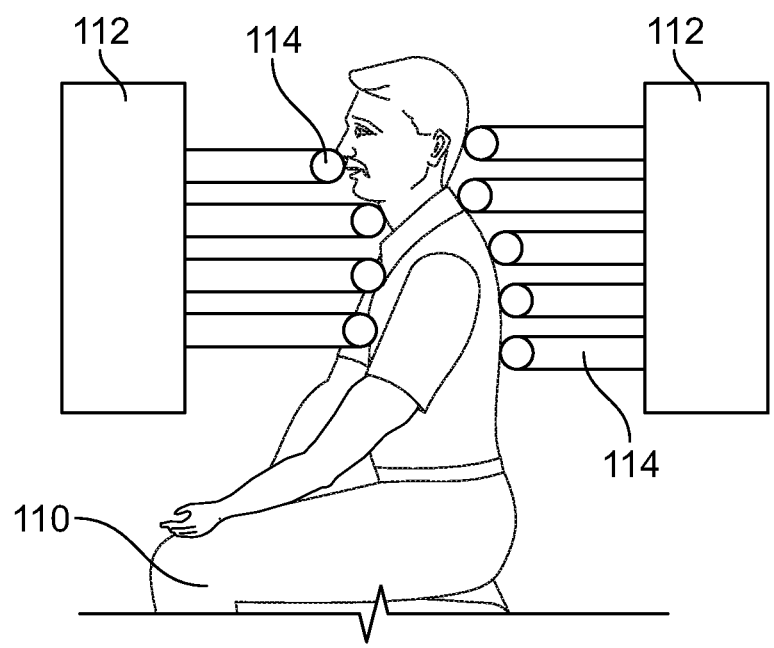
FIG. 12 is a schematic block diagram illustrating a configuration of detector units in accordance with an embodiment.

As other examples of variations, the support members 112 may be rotated such that the detector units 114 now move laterally inward and outward as shown in FIG. 12 instead of upwards and downwards. It should be noted that in some embodiments, the support members 112 are in a fixed position as shown in FIG. 12, which is 90 degrees offset from other embodiments described herein. In this embodiment, the detector units 114 similarly may be moved in proximity to the subject 110 (illustrated in a seated position) to perform, for example, a thyroid SPECT exam. It should be noted that in the various embodiments, one or more of the different types of motion may be provided for the different component parts. For example, in FIG. 12, the support members 112 may be configured to move as described in more detail herein.

Figure 13:
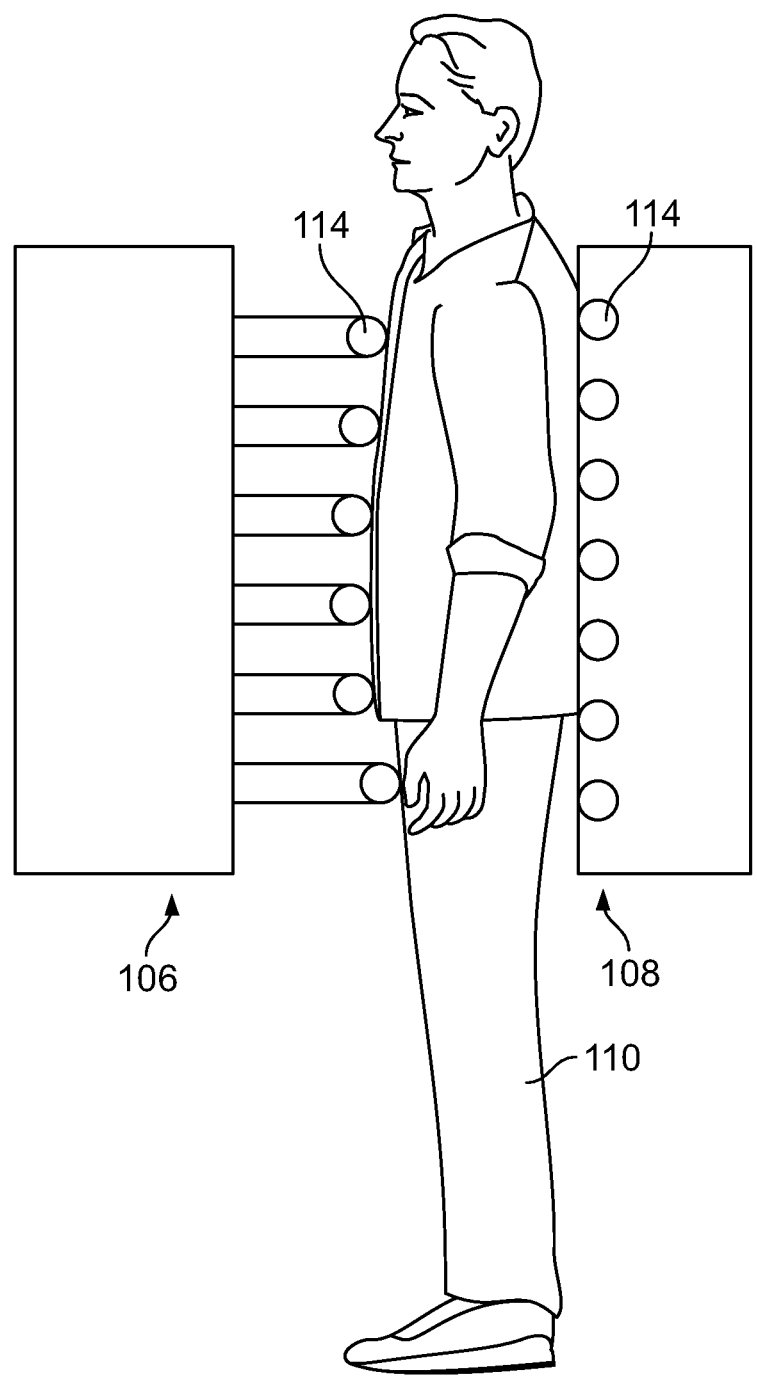
FIG. 13 is a schematic block diagram illustrating a configuration of detector units in accordance with another embodiment.

A similar configuration to FIG. 12 is illustrated in FIG. 13. In this embodiment, however, the subject 110 is standing. It should be noted that the support members 112 in this embodiment may move upwards or downwards. Additionally, in this embodiment, the detector units 114 of the detector array 108 are fixed (do not translate towards and away from the subject 110) and positioned adjacent a back of the subject 110. However, in other embodiments, as described in more detail herein, the detector units 114 of the detector array 108 may be configured to move (e.g., translate towards and away from the subject 110).

Figure 14:
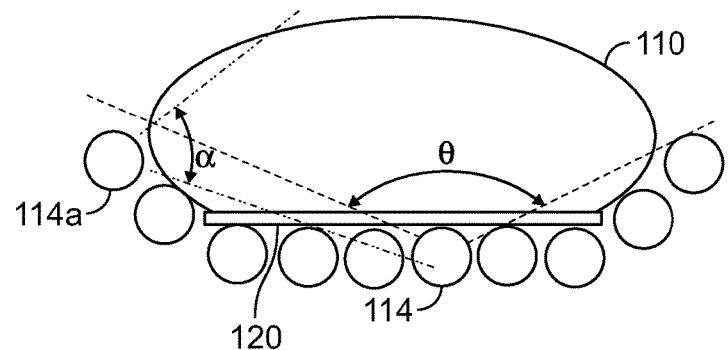
FIG. 14 is a schematic block diagram illustrating different rotational movement ranges for different detector units in accordance with an embodiment.

In some embodiments, the amount of rotation that the detector units 114 move may be different. For example, as illustrated in FIG. 14, the edge detector 114*a* may have limited (asymmetric) rotational movement range relative to other detector units 114, illustrated below the patient table 120. Thus, for example, an angle α corresponding to rotational movement of one or more of the detector units 114 may be smaller than the angle θ corresponding to the rotational movement of one or more of the other detector units 114.

Figure 15:
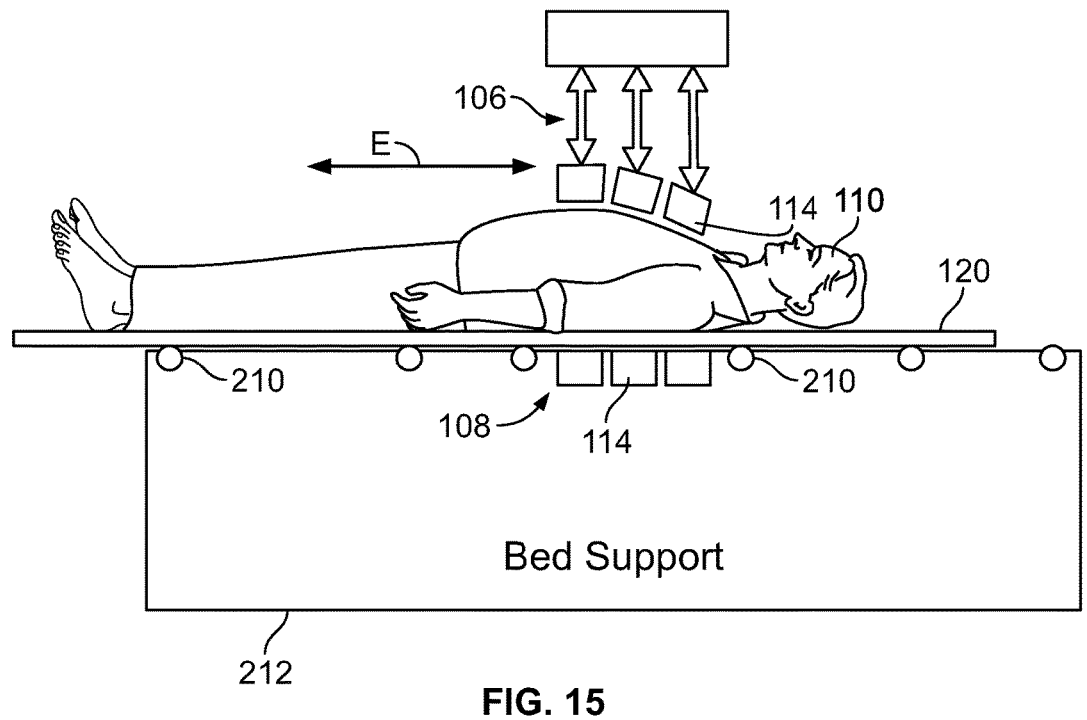
FIG. 15 is a schematic block diagram illustrating a configuration of detector units in accordance with another embodiment.

Other variations are contemplated. For example, as shown in FIG. 15, the detector units 114 of the detector array 106 may be movable as described herein and the detector units 114 of the detector array 108 may be fixed. However, in this embodiment, a plurality of rollers 210, which may be fixedly coupled to a table support 212 allow movement of the patient table 120 along a top of the table support 210. For example, the patient table 120 rolls along the rollers 210 to position the subject 110 at different axial positions along the examination axis (E). It should be noted that in this embodiment, the detector units 114 of the detector array 106 are capable of tilting motion as shown.

Figure 16:
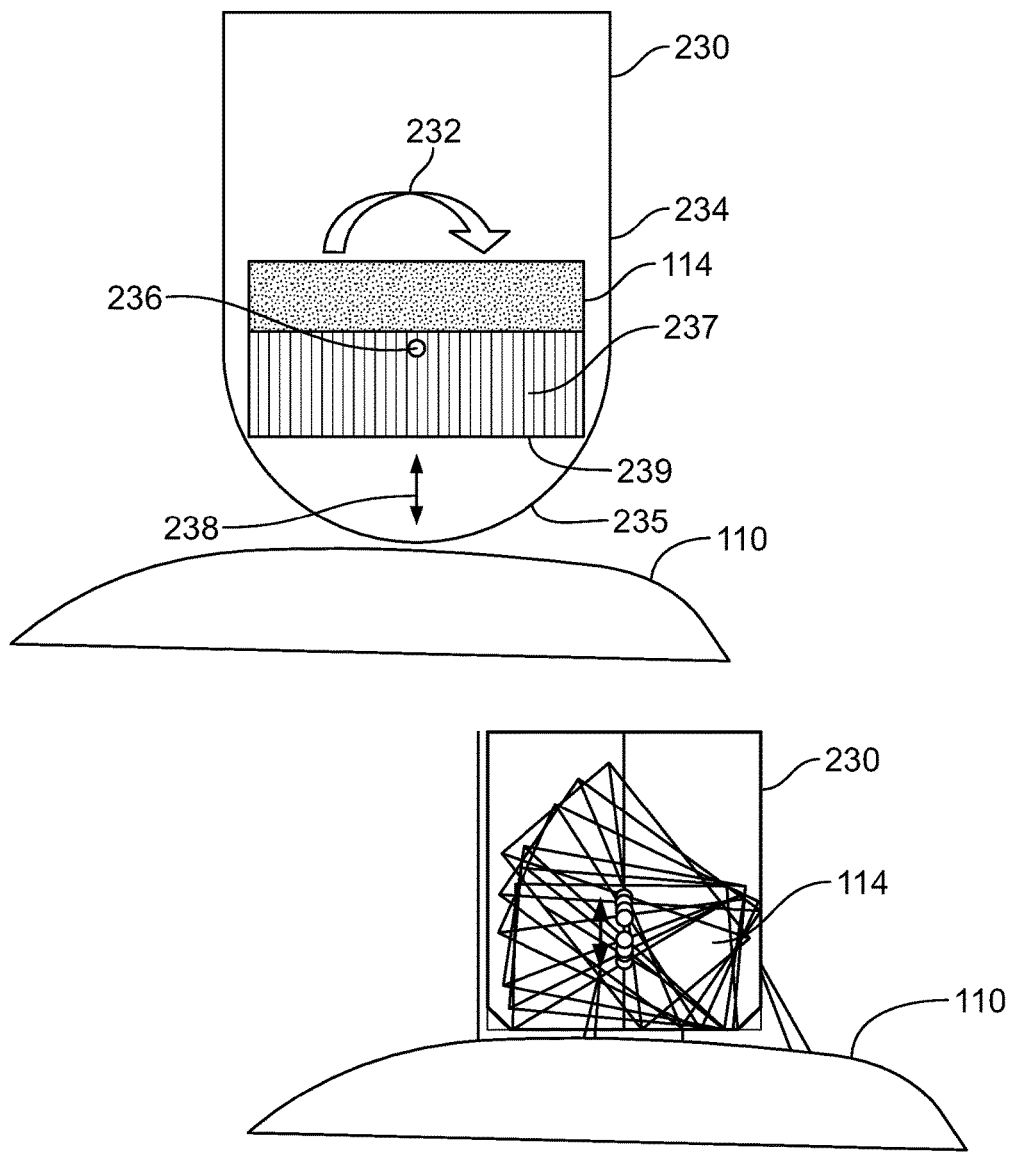
FIG. 16 is a schematic block diagram illustrating movement of a detector unit within a housing in accordance with an embodiment.

As illustrated in FIG. 16, the detector units 114 may be located within respective housings 230 which may be a cover over the entire detector unit 114. For example, the detector units 114 may be housed to protect the subject 110 from (the relatively rapid) pivoting motion (illustrated by the arrow 232) of the detector unit 114. The housing 230 may have a round cover (schematically depicted as the circular detector seen for example in FIGS. 2-14). In some embodiments, the housing 230 includes a cover 234 shaped with a section 235 of a cylinder that allows for the pivoting motion of the detector unit 114 around a pivoting point 236. When a flat collimator 237 is used, a gap 238 exists between the surface 239 of the collimator 237 and the subject 110. This gap 238 causes a reduction of the resolution and thus reduction of the image quality. In one embodiment, a range of motion of the detector unit 114 is provided within the housing 230, such as rotational and/or translational movement as shown. Thus, in this embodiment, the coordinated pivoting and up/down movement (lateral movement) of the detector units 114 is within the housing 230, reduces or eliminates a dead space or gap 238 between the detector and the subject 110.

Thus, various embodiments provide movable detector units that may be used for general purpose NM imaging, such as to define a general purpose gamma camera with arrays of heads each having linear motion and rotation.

Figure 17:
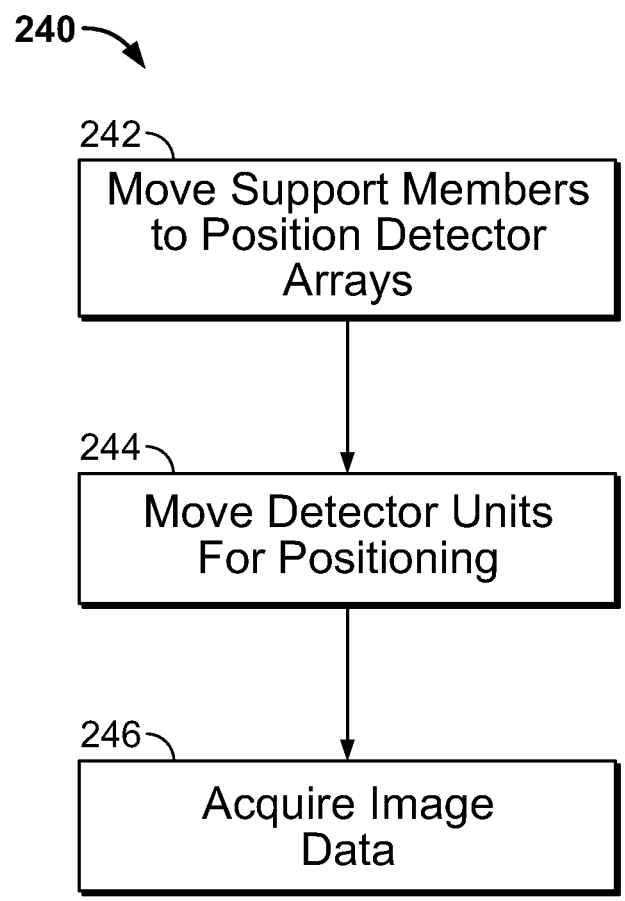
FIG. 17 is a flowchart of a method for controlling movement of detector units in accordance with various embodiments.

Some embodiments provide a method 240 as shown in FIG. 17 for general purpose NM imaging. The method includes moving at 242 one or more support members having detector units coupled thereto as an array. The movement positions the detector arrays with respect to a subject as described herein. This initial movement may provide a coarse positioning of the detector units relative to the subject. Thereafter, one or more of the detector units are moved at 244 as described herein to individually and independently position the detector unit(s) with respect to the subject. This movement may be a fine tuning movement in some embodiments to further position the detector units in close proximity to the subject (e.g., within 1-5 cm, however other distances may be used). Once positioned, image data is acquired at 246, which may include rotating the detector units as described herein. It should be noted that in some embodiments at least some of the imaging detectors 102 (or detector units 114) move towards and away from the subject 110 along substantially linear parallel directions. In some embodiments, at least some of detector units 114 move towards and away from the subject 110 along substantially linear opposing directions. The parallel motion reduces the likelihood of collision of two imaging detectors 102 or detector units 114 without having to calculate respective locations and control motion in a way that prevents such collision. Parallel motion of the imaging detectors 102 or detector unit 114 also provides that the lateral gaps (normal to the linear parallel motion) between two adjacent imaging detectors 102 or detector units 114 is fixed irrespective to motion towards or away from the subject 110. In some embodiments, the imaging detectors 102 or detector units 114 may be closely packed, such as in a closely packed "comb-like" array in order to obtain high system sensitivity that increases with the number of imaging detectors 102 or detector units 114 participating in the data acquisition. In contrast, a radially moving detector array is prone to detector collisions. Additionally, when imaging detectors 102 or detector units 114 move out radially large gaps between adjacent detectors may allow large portions of the radiation to escape detection.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Also, as used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
a gantry;
first and second detector arrays having at least five detector carriers coupled to the gantry, wherein the at least five detector carriers of the first and second detector arrays include a detector head positioned at a distal end that includes a solid state gamma detector and is configured to pivot, and the at least five detector carriers of the first and second detector arrays are configured to move in parallel with respect to each other towards a patient.

2. The imaging system of claim 1, wherein lateral gaps between the at least five detector carriers of the first and second detector arrays are fixed while moving in parallel.

3. The imaging system of claim 1, wherein the at least five detector carriers of the first and second detector arrays form a closed packed array.

4. The imaging system of claim 1, wherein the first and second detector arrays are positioned at opposing sides of the patient.

5. The imaging system of claim 1, further comprising a support member coupled to the first and second detector arrays, wherein the support member is configured to move the first and second detector arrays laterally with respect to the patient.

6. The imaging system of claim 1, wherein the at least five detector carriers of the first and second detector arrays are configured to move independent from each other.

7. The imaging system of claim 1, wherein detector heads of the at least five detector carriers of the first or second detector array are configured for coordinated pivoting and movement to reduce a gap between the solid state gamma detector and the patient.

8. The imaging system of claim 1, wherein the detector head is located within a housing having a cover, the cover being configured to have a shape that allows the detector head to rotate about a pivoting point.

9. The imaging system of claim 1, wherein a number of the at least five detector carriers of the first and second detector arrays that move is based on a size of the patient.

10. The imaging system of claim 1, wherein the detector head includes a collimator.

11. The imaging system of claim 1, further comprising a support member coupled to the first and second detector arrays, the at least five detector carriers of the first and second array are positioned at different radial positions around the patient, wherein the support member is configured to move the first and second detector arrays along the different radial positions.

12. An imaging system comprising:
a gantry;
at least five detector carriers coupled to the gantry configured to move linearly to a patient in parallel with respect to each other, wherein the at least five detector carriers include a detector head positioned at a distal end that includes a solid state gamma detector and is configured to pivot; and
at least two edge detector units positioned orthogonally with respect to the at least five detector carriers, the at least two edge detector units having a solid state gamma detector.

13. The imaging system of claim 12, wherein the at least two edge detector units are coupled to the gantry, the at least two edge detector units are configured to move laterally with respect to the patient.

14. The imaging system of claim 12, wherein a portion of the at least two edge detector units are in a fixed positon relative to the patient.

15. The imaging system of claim 12, wherein the gantry is configured to rotate the at least two edge detector units and the at least five detector carriers.

16. The imaging system of claim 15, wherein a first range of rotation of the at least five detector carriers is different than a second range of rotation of the at least two edge detector units.

17. The imaging system of claim 12, wherein the at least two edge detector units are positioned laterally with respect to the patient.

18. A method for medical imaging, the method comprising:
extending linearly in parallel first and second detector arrays with respect to each other to opposing sides of a patient from a gantry, wherein the first and second detector arrays having at least five detector carriers coupled to the gantry, the at least five detector carriers of the first and second detector arrays include a detector head positioned at a distal end that includes a solid state gamma detector and is configured to pivot; and
rotating at least a portion of the detector heads to adjust a proximity of the portion of the detector heads with respect to the patient.

19. The method of claim 18, further comprising acquiring image data during the rotating operation.

20. The method of claim 18, further comprising acquiring image data from the first and second detector arrays and at least two edge detector units positioned orthogonally with respect to the at least five detector carriers, the at least two edge detector units having a solid state gamma detector.

* * * * *